(12) United States Patent  
Carter

(10) Patent No.: US 7,018,809 B1  
(45) Date of Patent: Mar. 28, 2006

(54) EXPRESSION OF FUNCTIONAL ANTIBODY FRAGMENTS

(75) Inventor: Paul J. Carter, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/199,268

(22) PCT Filed: Sep. 18, 1992

(86) PCT No.: PCT/US92/07986

§ 371 (c)(1),
(2), (4) Date: Feb. 28, 1994

(87) PCT Pub. No.: WO93/06217

PCT Pub. Date: Apr. 1, 1993

Related U.S. Application Data

(63) Continuation-in-part of application No. 07/762,292, filed on Sep. 19, 1991, now abandoned.

(51) Int. Cl.
*C12P 21/06* (2006.01)

(52) U.S. Cl. .................... 435/69.1; 435/69.7; 435/70.1; 435/70.21; 435/172.3; 435/972; 530/389.1; 530/387.3

(58) Field of Classification Search .............. 530/387.1, 530/387.3; 435/69.6, 70.21, 172.3, 69.1, 435/325, 69.7, 70.1, 972
See application file for complete search history.

(56) References Cited

U.S. PATENT DOCUMENTS

| | | | |
|---|---|---|---|
| 4,444,878 A | 4/1984 | Paulus et al. | |
| 4,642,334 A | 2/1987 | Moore et al. | 530/387.3 |
| 4,816,567 A | 3/1989 | Cabilly et al. | |
| 4,946,778 A | 8/1990 | Ladner et al. | |
| 5,219,996 A | 6/1993 | Bodmer et al. | 526/262 |
| 5,274,119 A * | 12/1993 | Frasier et al. | 548/521 |
| 5,618,920 A | 4/1997 | Robinson et al. | 530/387.1 |
| 5,648,237 A | 7/1997 | Carter | 435/69.1 |
| 5,698,417 A | 12/1997 | Robinson et al. | 435/69.1 |
| 5,698,435 A | 12/1997 | Robinson et al. | 435/328 |

FOREIGN PATENT DOCUMENTS

| | | |
|---|---|---|
| AU | A-27617/88 | 6/1989 |
| AU | B-57621/90 | 1/1991 |
| EP | 136907 | 4/1985 |
| EP | 0338745 | 10/1989 |
| EP | 459 577 | 12/1991 |
| WO | WO 89/01783 | 3/1989 |
| WO | WO 89/01974 | 3/1989 |
| WO | WO 89/06692 | 7/1989 |
| WO | WO 92/01059 | 1/1992 |
| WO | WO 92/10209 | 6/1992 |
| WO | WO 92/22324 | 12/1992 |
| WO | WO 93/12220 | 6/1993 |

OTHER PUBLICATIONS del Rosario RB, et al, 1990, Bioconjugate Chemsitry, 1(1): 51–59.*
Gillies, S et al. Human Alatihod. & Hybridousas 1(1):47–54, 1990.*
Spiegelberg, HL. Biochem. 10:2157–2163, 1975.*
Rodrigues, M. L. et al. J. Immunol. 151:6954–6961, 1993.*
Sambrook et al. Molecular Cloning. Cold Spring Haron Lab. Press. Cold Spring Harbor. pp. 17.31–17.33, 1989.*
Tgo et al. Journal of Immunology p. 2595 vol. 143, 1989.*
Hashida et al. Journal of Applied Biochem. 6 56–63 (1984).*
Johnston et al. Immunochemistry 1982 Blackwell Scientific Publication.*
Voet et al., "Protein Isolation" *Biochemistry*, John Wiley and Sons, Inc. pp. 76–77 (1990).
Better and Horwitz, "Expression of engineered antibodies and antibody fragments in microorganisms" *Methods in Enzymology* 178:476–496 (1989).
Better et al., "*Escherichia coli* secretion of an active chimeric antibody fragment" *Science* 240:1041–1043 (1988).
Better et al., "Potent anti–CD5 ricin A chain immunoconjugates from bacterially produced Fab' and F(ab')$_2$" *Proc. Natl. Acad. Sci. USA* 90:457–461 (1993).
Better et al., "Production and Scale Up of Chimeric Fab Fragments from Bacteria" *Advances in Gene Technology: The Molecular Biology of Immune Diseases & the Immune Response* (ICSU Short Rpts.), Streilein et al., eds. vol. 10:105 (1990).
Bird et al., "Single–chain antigen–binding proteins" *Science* 242:423–426 (1988).
Boss et al., "Assembly of functional antibodies from immunoglobulin heavy and light chains synthesised in *E. coli*" *Nucleic Acids Research* 12(9):3791–3806 (1984).
Brennan et al., "Preparation of bispecific antibodies by chemical recombination of monoclonal immunoglobulin $G_1$ fragments" *Science* 229:81–83 (1985).

(Continued)

*Primary Examiner*—Susan Ungar
*Assistant Examiner*—Minh-Tam Davis
(74) *Attorney, Agent, or Firm*—Merchant & Gould P.C.

(57) ABSTRACT

Methods for the high yield production of antibody Fv-containing polypeptides, especially Fab' and F(ab')$_2$ antibody fragments are provided. Expression of heavy and light chain Fv in a microbial secretory system is followed by recovery of Fv from the periplasm under conditions that maintain a cysteine residue as a free thiol. The free thiol is reacted with free thiol of an antibody fragment of the same or differing specificity, or with agents such as diagnostic labels or therapeutic moieties. The products offer advantages of homogeneity and purity not available through the use of known methods for preparing such derivatives.

11 Claims, 2 Drawing Sheets

OTHER PUBLICATIONS

Burgess et al., "Possible Dissociation of the Heparin–binding and Mitogenic Activities of Heparin binding (Acidic Fibroblast) Growth Factor–1 from Its Receptor–binding Activities by Site–directed Mutagenesis of a Single Lysine Residue" *Journal of Cell Biology* 111:2129–2138 (1990).

Cabilly et al., "Generation of antibody activity from immunoglobulin polypeptide chains produced in *Escherichia coli*" *Proc. Natl. Acad. Sci. USA* 81:3273–3277 (1984).

Cabilly, Shmuel, "Growth at sub–optimal temperatures allows the production of functional, antigen–binding Fab fragments in *Escherichia coli*" *Gene* 85:553–557 (1989).

Carter et al., "High level *escherichia coli* expression and production of a bivalent humanized antibody fragment" *Bio/Technology* 10:163–167 (1992).

Carter et al., "Humanization of an anti–p185$^{HER2}$ antibody for human cancer therapy" *Proc. Natl. Acad. Sci.* 89:4285–4289 (1992).

Carter, P. and Wells, J.A., "Engineering enzyme specificity by "substrate–assisted catalysis"" *Science* 237:394–399 (1987).

Chothia, Cyrus, "Domain association in immunoglobulin molecules: The packing of variable domains" *J. Mol. Biol.* 186:651–663 (1985).

Condra et al., "Bacterial expression of antibody fragments that block human rhinovirus infection of cultured cells" *Journal of Biological Chemistry* 265(4):2292–2295 (1990).

Cumber et al., "Comparative stabilities in vitro and in vivo of a recombinant mouse antibody FvCys fragment and a bisFvCys conjugate" *J. Immunol.,* 149(1):120–126 (1992).

Fanger et al., "Bispecific antibodies and targeted cellular cytotoxicity" *Immunology Today* 12(2):51–54 (1991).

Fendly et al., "Characterization of murine monoclonal antibodies reactive to either the human epidermal growth factor receptor or HEM2/neu gene product" *Cancer Research* 50(5):1550–1558 (Mar. 1, 1990).

Gavit et al., "Purification of a Mouse–Human Chimeric Fab Secreted from *E. coli*" *BioPharm* pp. 28–29, 32–34, 58 (1992).

Gilles et al., "Antigen binding and biological activities of engineered mutant chimeric antibodies with human tumor specificities" *Hum. Antibod. Hybridomas* 1(1):47–54 (1990).

Glennie et al., "Preparation and Performance of Bispecific F(ab'γ)$_2$ Antibody Containing Thioether–Linked Fab'γ Fragments" *J. Immunol.* 139(7):2367–2375 (1987).

Glennie M.J. et al., "Bispecific F(ab'γ)$_2$ antibody for the delivery of saporin in the treatment of lymphoma" *J. Immunol.* 141(10):3662–3670 (1988).

Glockshuber et al., "A Comparison of Strategies to Stabilize Immunoglobulin F$_v$–Fragments" *Biochemistsry* 29:1362–1367 (1990).

Hammerling et al., "Use of hybrid antibody with anti–γG and anti–ferritin specificities in locating cell surface antigens by electron microscopy" *Journal of Experimental Medicine* 128:1461–1469 (1968).

Hasemann and Capra, "High–level production of a functional immunoglobulin heterodimer in a baculovirus expression system" *Proc. Natl. Acad. Sci. USA* 87:3942–3946 (1990).

Horwitz et al., "Secretion of functional antibody and Fab fragment from yeast cells" *Proc. Natl. Acad. Sci. USA* 85:8678–8682 (1988).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165–1172 (1989).

Huse et al., "Generation of a large combinatorial library of the immunoglobulin repertoire in phage lambda" *Science* 246:1275–1281 (1989).

Huston et al., "Protein engineering of antibody binding sites: Recovery of specific activity in an anti–digoxin single–chain Fv analogue produced in *Escherichia coli*" *Proc. Natl Acad. Sci. USA* 85:5879–5883 (1988).

Kabat et al. *Sequences of Proteins of Immunological Interest,* Bethesda, MD:National Institutes of Health pp. iii–xxvii, 41–176 (1987).

King et al., "Tumor Localization of Engineered Antibody Fragments" *Antibody. Immunoconjugates. & Radiopharmaceuticals* 5(2):159–170 (1992).

Lazar et al., "Transforming Growth Factor α: Mutation of Aspartic Acid 47 and Leucine 48 Results in Different Biological Activities" *Molecular & Cellular Biology* 8(3):1247–1252 (1988).

Liu et al., "Heteroantibody duplexes target cells for lysis by cytotoxic T lymphocytes" *Proc. Natl. Acad. Sci. USA* 82:8648–8652 (1985).

Lupu et al., "Direct interaction of a ligand for the erB2 oncogene product with the EGF receptor and p185$^{erbB2}$" *Science* 249(4976):1552–1555 (Sep. 28, 1990).

Lyons et al., "Site–specific attachment to recombinant antibodies via introduced surface cysteine residues" *Protein Engineering* 3(8):703–708 (1990).

McCafferty et al., "Phage antibodies: filamentous phage displaying antibody variable domains" *Nature* 348:552–554 (Dec. 6, 1990).

Miller, S., "Protein–protein recognition and the association of immunoglobulin constant domains" *J. Mol. Biol.* 216:965–973 (1990).

Milstein & Cuello, "Hybrid hybridomas and their use in immunohistochemistry" *Nature* 305:537–540 (1983).

Morrison, S. L. et al., "Chimeric human antibody molecules: mouse antigen–binding domains with human constant region domains" *Proc. Natl. Acad. Sci. USA* 81(21):6851–6855 (Nov. 1984).

Neuberger et al., "Recombinant antibodies possessing novel effector functions" *Nature* 312(5995):604–608 (Dec. 1984).

Nisonoff and Mandy, "Quantitative estimation of the hybridization of rabbit antibodies" *Nature* 4826:355–359 (1962).

Nitta et al., "Preliminary trial of specific targeting therapy against malignant glioma" *Lancet* 335(8686):368–371 (Feb. 17, 1990).

Nitta, T. et al., "Bispecific F(ab')$_2$ monomer prepared with anti–CD3 and anti–tumor monoclonal antibodies is most potent in induction of cytolysis of human T cells" *European Journal of Immunology* 19:1437–1441 (1989).

Nolan et al., "Bifunctional antibodies: concept, production and applications" *Biochimica et Biophysica Acta* 1040:1–11 (1990).

Novotny and Haber, "Structural invariants of antigen binding: comparison of immunoglobulin V$_L$–V$_H$ and V$_L$–V$_L$ domain dimers" *Proc. Natl. Acad. Sci. USA* 82(14):4592–4596 (Jul. 1985).

Padlan et al., "Antibody Fab assembly: the interface residues between CH1 and CL" *Molecular Immunology* 23(9):951–960 (1986).

Pantoliano et al., "Protein engineering of subtilisin BPN': Enhanced stabilization through the introduction of two cysteines to form a disulfide bond" *Biochemistry* 26:2077–2082 (1987).

Parham, "Preparation and purification of active fragments from mouse monoclonal antibodies" *Handbook of Experimental Immunology*, Weir E.M. (ed.), 4th edition, CA:Blackwell Scientific, Chapter 14, vol. 1:14.1–14.23 (1986).

Parham, Peter, "In Vitro produciton of a hybrid monoclonal antibody that preferentially binds to cells that express both HLA–A2 and HLA–B7" *Human Immunology* 12:213–221 (1985).

Paulus, H., "Preparation and Biomedical Applications of Bispecific Antibodies" *Behring Inst. Mitt.* 78:118–132 (1985).

Perez et al., "Specific targeting of cytotoxic T cells by anti–T3 linked to anti–target cell antibody" *Nature* 316:354–356 (1985).

Pluckthun and Skerra, "Expression of functional antibody Fv and Fab fragments in *Escherichia coli*" *Methods in Enzymology* 178:497–515 (1989).

Pluckthun et al., "Engineering of antibodies with a known three–dimensional structure" *Cold Spring Harbor Symposia on Quantitative Biology*, Cold Spring Harbor Laboratory vol. LII:105–112 (1987).

Pluckthun, Andreas, "Antibody engineering: advances from the use of *escherichia coli* expression systems" *Biotechnology* 9:545–51 (1991).

Putlitz et al., "Antibody production in baculovirus–infected insect cells" *Bio/Technology* 8:651–654 (1990).

Raso and Griffin, "Hybrid antibodies with dual specificity for the delivery of ricin to immunoglobulin–bearing target cells" *Cancer Research* 41:2073–2076 (1981).

Reichmann et al., "Expression of an antibody Fv fragment in myeloma cells" *J. Mol. Biol.* 203:825–828 (1988).

Skerra and Pluckthun, "Assembly of functional immunoglobulin $F_v$ fragment in *escherichia coli*" *Science* 240:1038–1041 (1988).

Skerra et al., "Secretion and in vivo folding of the Fab fragment of the antibody McPC603 in *Escherichia coli*: influence of disulphides and cis prolines" *Protein Engineering* 4(8):971–979 (1991).

Takeda et al., "Construction of chimaeric processed immunoglobulin genes containing mouse variable and human constant region sequences" *Nature* 314(6010):452–454 (Apr. 1985).

Ward, E.S. et al., "Binding activities of a repertoire of single immunoglobulin variable domains secreted from *Escherichia coli*" *Nature* 341:544–546 (1989).

Zemel–Dreasen et al., "Secretion and processing of an immunoglobulin light chain in *Escherichia coli*" *Gene* pp. 315–322 (1984).

Mandy et al., "Recombination of Univalent Subunits Derived from Rabbit Antibody" *The Journal of Biological Chemistry* 236(12):3221–3226 (Dec. 1961).

Rodrigues et al., "Engineering Fab' Fragments for Efficient $F(ab)_2$ Formation in *Escherichia coli* and for Improved In Vivo Stability" *The Journal of Immunology* 151(12):6954–6961 (Dec. 15, 1993).

Axelsson K., "Bacterial Lipopolysaccharides and Glutathione Mixed Disulfides as Possible Contaminants of Human Growth Hormone Produced with the Use of *E. coli* K12" *Acta Chemica Scandinavica, Series B* 39(1):69–77 (1985).

Morrison et al., "Genetically Engineered Antibody Molecules and Their Application" *Biological Approaches to the Controlled Delivery of Drugs*, Annals of the New York Academy of Sciences, New York, New York:The New York Academy of Sciences vol. 507:187–198 (1987).

Morrison et al., "Production and Characterization of Genetically Engineered Antibody Molecules" *Clinical Chemistry* 34(9):1668–1675 (1988).

Jungbauer et al., "Pilot scale production of a human monoclonal antibody against human immunodeficiency virus HIV–1" *Journal of Biochemical and Biophysical Methods* 19:223–240 (1989).

\* cited by examiner

EXPRESSION OF FUNCTIONAL ANTIBODY FRAGMENTS

This application is a 371 of PCT/US92/07986 filed Sep. 18, 1992, which is a continuation-in-part of U.S. Ser. No. 07/762,292 filed Sep. 19, 1991 (abandoned).

FIELD OF THE INVENTION

This invention relates to the production of functional antibody fragments in a microbial host.

BACKGROUND OF THE INVENTION

Naturally occurring antibodies (immunoglobulins) comprise two heavy chains linked together by disulfide bonds and two light chains, each light chain being linked to one of the heavy chains by disulfide bonds. Each chain has an N-terminal variable domain ($V_H$ or $V_L$) and a constant domain at its C-terminus; the constant domain of the light chain is aligned with and disulfide bonded to the first constant domain of the heavy chain, and the light chain variable domain is aligned with the variable domain of the heavy chain. The heavy chain constant region includes (in the N- to C-terminal direction) the $C_H1$ and hinge regions. The light chain also contains a hinge domain. Particular amino acid residues are believed to form an interface between and disulfide bond the light and heavy chain variable domains, see e.g. Chothia et al., *J. Mol. Biol.* 186:651–663 (1985); Novotny and Haber, *Proc. Natl. Acad. Sci. USA* 82:4592–4596 (1985); Padlan et al., *Mol. Immunol.*, 23(9): 951–960 (1986); and S. Miller, *J. Mol. Biol.*, 216: 965–973 (1990).

The constant domains are not involved directly in binding the antibody to an antigen, but are involved in various effector functions, such as participation of the antibody in antibody-dependent cellular cytotoxicity and complement dependent cytotoxicity. The variable domains of each pair of light and heavy chains are involved directly in binding the antibody to the antigen. The domains of natural light and heavy chains have the same general structure, the so-called immunoglobulin fold, and each domain comprises four framework (FR) regions, whose sequences are somewhat conserved, connected by three hyper-variable or complementarity determining regions (CDRs) (see Kabat, E. A. et al., *Sequences of Proteins of Immunological Interest*, National Institutes of Health, Bethesda, Md., (1987)). The four framework regions largely adopt a β-sheet conformation and the CDRs form loops connecting, and in some cases forming part of, the β-sheet structure. The CDRs in each chain are held in close proximity by the framework regions and, with the CDRs from the other chain, contribute to the formation of the antigen binding site.

Antibodies can be divided into a variety of antigen-binding fragments. The $F_v$ fragment is a heterodimer containing only the variable domains of the heavy chain and the light chain. The Fab fragment also contains the constant domain of the light chain and the first constant domain ($C_H1$) of the heavy chain. Fab' fragments differ from Fab fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which are between hinge cysteines.

Recombinant production of antibodies and antibody fragments facilitates the engineering of antibodies with enhanced antigen binding affinities, modified immunogenicity, and also of bifunctional antibodies. The first expression systems reported with which functional antibodies could obtained were for mammalian cells. The U.S. patent of Cabilly et al., U.S. Pat. No. 4,816,567, for example, teaches a method of co-expressing at least the variable region sequences of light and heavy chains in host cells. Other researchers in the field have reported baculovirus expression systems (Haseman et al., *Proc. Natl. Acad. Sci. USA* 87:3942–3946 (1990), yeast systems (Horwitz et al., *Proc. Natl. Acad. Sci. USA*, 85:8678–8682 (1988), combinatorial libraries in phage lambda (Huse et al., *Science* 246:1275–1281 (1989), and work with filamentous phage (McCafferty et al., *Nature* 348:552–554 (1990).

The production of antibodies and antibody fragments in bacterial systems have been pursued by workers in the field, particularly in *E. coli* expression systems. There are several advantages to *E. coli* expression systems, including a well-studied and convenient gene technology which permits constructs to be made easily and directly expressed, and the relatively convenient and economical large-scale production of product made possible by the fast growth of *E. coli* and its comparatively simple fermentation. The large-scale production of functional antibody fragments in *E. coli* would be valuable for research as well as commercial applications.

The expression of antibody genes in bacteria was reported by Cabilly et al., *Proc. Natl. Acad. Sci. USA* 81:3273–3277 (1984), Boss et al., *Nucleic Acids Res.* 12:3791–3806 (1984); these reports show cytoplasmic expression and rather variable yields were reported. Zemel-Oreasen et al., *Gene* 315–322 (1984) report the secretion and processing of an immunoglobulin light chain in *E. coli*. Plückthun et al., *Cold Spring Harbor Symposia on Quantitative Biology*, Volume LII, pages 105–112 (1987, Cold Spring Harbor Laboratory) disclose expression of a cytoplasmic hybrid protein, a potentially exportable hybrid protein, and expression and periplasmic transport of $V_L$, $V_H$, $V_L C_L$, and $V_H C_H$ chains as fusions with an alkaline phosphatase or β-lactamase signal sequences. Skerra and Plückthun, *Science* 240:1038–1041 (1988) report the periplasmic secretion and correct folding in vivo of the variable domains of an antibody to the *E. coli* periplasm; a similar strategy and results were reported by Better et al., *Science* 240:1041–1043 (1988) for expression of a murine Fab fragment.

Bird et al., *Nature* 332:323–327 (1989) report the linkage of the light and heavy chain fragment of the Fv region via an amino acid sequence, and production of the complex as a single polypeptide in *E. coli*; see also Ladner et al., U.S. Pat. No. 4,946,778. Huston et al., *Proc. Natl. Acad. Sci. USA* 85:5879–5883 (1988) report similar work. Ward et al., *Nature* 341:544–546 (1989) report the production in and secretion of "single-domain" antibodies (isolated heavy chain variable domains) from *E. coli*. Condra et al., *Journal of Biological Chemistry*, 265(4):2292–2295 (1990) disclose the expression of cDNAs encoding antibody light and heavy chains in *E. coli* and their renaturation into Fab fragments. Better and Horwitz, *Methods in Enzymology*, 178:476–496 (1989), describe the expression, and secretion of functional Fab fragments from *E. coli* and *Saccharomyces cerevisiae*.

Plückthun and Skerra describe techniques for the expression of functional antibody Fv and Fab fragments in *E. coli* in *Methods in Enzymology* 178:497–515 (1989). According to their strategy, in the cytoplasm, the precursor proteins for $V_L$ and $V_H$, each fused to a bacterial signal sequence, are synthesized in reduced form. After translocation through the inner membrane into the periplasm, the signal sequences are cleaved, the domains fold and assemble, and the disulfide bonds form. They teach that expression of the Fab fragment according to their strategy is analogous. Similar expression strategies are found elsewhere in the literature. See also Plückthun, *Biotechnology*, 9:545–551 (1991) for a review of *E. coli* expression of antibody fragments.

Cabilly (*Gene*, 85:553–557 [1989]) teaches that, in *E. coli* cells growing at reduced temperatures (21° C. or 30° C., rather than at 37° C.), a single expression plasmid coding for kappa-chains and truncated heavy chains (Fd fragments) gives rise to high yields of functional Fab fragments. Cabilly discusses that the Fab fragments seem to exist in the *E. coli* cytoplasm as non-covalently linked dimers, but that soluble Fab fragments isolated from *E. coli* appear as covalent dimers, formed by air oxidation following cell rupture.

It is known in the literature that in the presence of low concentrations of a mild reductant such as cysteamine the bivalent $F(ab')_2$ antibody fragment dissociates into two Fab' fragments. This dissociation is reversible by mild oxidation. The production of Fab and $F(ab')_2$ antibody fragments has also been shown by partial reduction and limited proteolysis of intact antibodies, see e.g. Parham, in *Cellular Immunology* (E. M. Weir, Ed., Blackwell Scientific, CA) 4th edition, vol. 1 chapter 14 (1983), however with these methods it is difficult to control the precise nature and proportions of the antibody fragment recovered. Bivalent antibodies are those which contain at least two epitopic combining sites (which sites may be on the same or different antigens).

Bispecific antibodies are bivalent antibodies capable of binding two epitopes not shared by a single antigen. Bispecific monoclonal antibodies (BsMAbs) with dual specificities for tumor-associated antigens on tumor cells and for surface markers in immune effector cells have been described (see, e.g. Liu et al., *Proc. Natl. Acad. Sci. USA* 82:8648 (1985): Perez et al., *Nature* 316:354 (1985)). These BsMAbs have been shown to be effective in directing and triggering effector cells to kill tumor cell targets (Fanger et al., *Immunol. Today* 12:51 (1991)). One approach to the production of BsMabs involves the fusion of two monoclonal antibody-producing hybridomas to form quadromas (hybrid hybridomas) which secrete BsMab in addition to undesirable chain combinations including parental MAbs (Milstein, C. and Cuello, A. C., *Nature*, 305:537 [1983]). However, for production of bispecific humanized antibodies and antibody fragments, other techniques would be preferred.

Nisonoff and Mandy (*Nature* 4826:355–359 (1962)) describe the digestion of rabbit antibodies and subsequent recombination of the antibody fragments; they disclose that antibody molecules of dual specificity can be obtained by combining univalent fragments of pepsin-treated antibodies of different specificities. See also Hammerling et al., *Journal of Experimental Medicine* 128:1461–1469 (1968); Parham, *Human Immunology* 12:213–331 (1985); Raso and Griffin, *Cancer Research* 41:2073–2076 (1981); and Paulus (U.S. Pat. No. 4,444,878).

Another approach utilizes directed chemical coupling of bispecific Fab' fragments from two different MAbs to assemble a BsMAb, in this case a $F(ab')_2$, with the desired specificities (see e.g., Nolan et al., *Biochimica et Biophysica Acta* 1040:1 (1990). See also R. A. Maurer's Ph.D. Thesis, Harvard University (1978), and Brennan et al., *Science* 229:81–83 (1985) for chemistries for the directed coupling of dithionitrobenzoate derivatives of Fab' fragments. Brennan et al. also teach the use of use sodium arsenite to cross-link two proximate cysteines, however this reaction involves highly toxic compounds. (Glennie et al., *J. Biol. Chem.*, 141(10): 3662–3670 [1985] and *J. Immunol.*, 139:2367–2375 [1975]) teach the preparation of bispecific $F(ab')_2$ antibody fragments containing thioether linkages. These chemistries would also be applicable for the coupling of identical Fab' fragments.

Lyons et al., *Protein Engineering* 3(8)703–708 (1990) teach the introduction of a cysteine into an antibody (there the $C_H1$ domain of a heavy chain) and the site-specific attachment of effector or reporter molecules through the introduced cysteine.

Despite the advances in *E. coli* expression of functional antibody fragments shown in the literature, there remains a need for efficient and economical techniques for the production of bivalent antibodies, particularly $F(ab')_2$ molecules, and for methods which permit the tailoring of bivalent and bispecific $F(ab')_2$ molecules. It would be desirable to produce stable Fab'-SH polypeptides which may be conveniently coupled in vitro to form bivalent Fv or $F(ab')_2$ molecules.

It is therefore an object of this invention to provide methods for the preparation of polypeptides comprising Fv domains, particularly Fab', Fab'-SH and $F(ab')_2$ antibody fragments, in or derived from bacterial cell culture in high yield.

It is a further object of this invention to provide methods for the efficient preparation of homogenous bivalent and bispecific $F(ab')_2$ antibody fragments.

It is another object of this invention to provide Fab' antibody fragments having at least one hinge region cysteine present as a free thiol (Fab'-SH). It is a related object to obviate the inherent problems in generating Fab'-SH from intact antibodies: differences in susceptibility to proteolysis and non-specific cleavage, low yield, as well as partial reduction which is not completely selective for the hinge disulfide bond(s). It is another object of the present invention to prevent intra-hinge disulfide bond formation without resorting to the use of highly toxic arsenite to chelate vicinal thiols, or other inefficient and undesirable methods.

Other objects, features, and characteristics of the present invention will become apparent upon consideration of the following description and the appended claims.

SUMMARY OF THE INVENTION

The principal embodiments of this invention are based on the surprising identification of cysteinyl free thiol in cysteinyl residues located outside of the light-heavy chain interface of recombinant microbial periplasmic antibody fragments, and the surprising discovery that Fv variants can be produced which contain only a single cysteinyl residue in the free thiol form. This facilitates the preparation of homogeneous recombinant $F(ab')_2$ and other Fv-containing bivalent polypeptides. Accordingly, in one embodiment this invention comprises expressing and secreting into the periplasm of a recombinant microbial cell culture a Fv polypeptide containing an immunoglobulin heavy chain Fv region and an immunoglobulin light chain Fv region, said light or heavy chain also comprising an unpaired cysteinyl residue as a free thiol, and recovering said polypeptide under conditions that substantially maintain said cysteinyl residue as the free thiol.

It will be understood that either of the Fv light or heavy chains optionally is fused to a polypeptide sequence which contains one or more cysteinyl residues, provided that at least one of such cysteinyl residues located in the domain C-terminal to either of the light or heavy chain Fv is present as the free thiol in the periplasm. Suitable polypeptide sequences include but are not limited to sequences derived from immunoglobulins, carrier proteins, receptors, growth factors, nutrient substances, cellular adhesive molecules, tissue-specific adhesion factors, enzymes, toxins and the like. Typically, an unpaired cysteinyl residue is substituted at the C-terminus of either the light or the heavy chain Fv domain or at the C-terminus of the light chain or heavy chain CH1 domain. The fused polypeptide sequence may comprise only the cysteinyl residue, or the cysteinyl residue can be present in a polypeptide fused to the C-terminus of (1) one of the Fv domains, (2) the light chain constant region or (3) the CH1 domain of a heavy chain. In the latter instance, the FV-CH1 domain is fused to a hinge region bearing a single free thiol cysteinyl residue, and preferably a hinge region amino acid sequence variant containing only a single cysteinyl residue. However, any other sequence containing a single free thiol cysteinyl residue is useful in place of the immunoglobulin hinge region.

In other embodiments, the Fv-CH1 domain is fused to a hinge region bearing more then one, typically two or three, free thiol residues, preferably a hinge region amino acid sequence variant containing two or more cysteinyl residues. For example, Fab'-SH amino acid sequence variants which have been modified to contain three cysteinyl residues may be produced recombinantly in a suitable host cell, for example CHO cells or *E. coli*, and are conveniently coupled in vivo by the host cell to form F(ab')$_2$ with three disulfide bonds connecting the heavy chains.

More particularly, the objects of this invention are accomplished by a method for the production of a Fab' antibody polypeptide having at least one hinge region cysteine present as a free thiol (Fab'-SH), comprising the steps of:

a. expressing nucleic acid encoding an immunoglobulin presequence comprising Fab' in a microbial host cell culture transformed with a vector comprising said nucleic acid operably linked to control sequences recognized by the host cell transformed with the vector, under conditions suitable for the secretion of Fab' to the periplasmic space of the host cell and formation of Fab'-SH; and b. recovering Fab'-(SH)$_n$ from said host cell, where n is greater than or equal to one.

Additional embodiments of the method of this invention comprise the subsequent recovery (including purification) of the Fab'-SH under conditions suitable for maintaining the hinge cysteinyl thiol(s) in protonated form. In certain embodiments, a metal ion chelating agent and/or a protease inhibitor is present during the culturing of the transformed cell or in the recovery of the Fab'-SH.

Optionally, the Fab'-SH is released from the host by freeze-thawing the host cell, subjecting it to osmotic shock, preparing a cell paste and purifying the Fab'-SH from the cell paste. Optionally, release of Fab'-SH from the host cell is facilitated by enzymatic digestion of the cell e.g., using lysozyme or physical disruption, e.g., by sonication or by use of a French press.

The Fv or polypeptide fused to the Fv (typically the hinge sequence) is modified in certain embodiments so that only one cysteinyl residue is present which, in the periplasm, exhibits free thiol. Thus, for example, the Fab amino acid sequence is modified by deleting or substituting all of the hinge sequence cysteinyl residues C-terminal to the first cysteine. Similarly, to obtain embodiments where, for example, three cysteinyl residues are to be present as the free thiol form, all of the hinge sequence cysteinyl residues C-terminal to the third cysteine are modified by deletion or substitution.

This invention also provides Fv, Fab', Fab'-SH and F(ab')$_2$ polypeptides which do not have a disulfide bond between the light and heavy chains. These polypeptides are referred to herein as "linkless". For example, the amino acid sequence of the polypeptide is modified by substituting or deleting one or, preferably, both of the two cysteines which form the inter-chain (heavy-light) disulfide bond. Typically, these cysteines are replaced with serines, although it is within the scope hereof to covalently modify one or both of the cysteine side chain so as to be incapable of forming a disulfide bond. In certain embodiments, there is a very strong interaction between the light and heavy chains such that eliminating the interchain disulfide does not result undesirable levels of dissociation between the light and heavy chains. The linkless Fab'-SH polypeptides advantageously allow homogeneous F(ab'), to be prepared by chemical coupling.

In another aspect, a method for the preparation of a polypeptide comprising F(ab')$_2$ comprises the steps of:

a. expressing nucleic acid encoding an immunoglobulin presequence comprising a first Fab' in a microbial host cell culture transformed with a vector comprising the nucleic acid operably linked to control sequences recognized by the host cell transformed with the vector, under conditions suitable for the secretion of said first Fab' to the periplasmic space of the host cell and formation of Fab'-SH, said first Fab' being capable of binding a first epitope;

b. expressing nucleic acid encoding an immunoglobulin presequence comprising a second Fab' in a microbial host cell culture transformed with a vector comprising the nucleic acid operably linked to control sequences recognized by the host cell transformed with the vector, under conditions suitable for the secretion of said second Fab' to the periplasmic space of the host cell and formation of Fab'-SH, said second Fab' being capable of binding a second epitope;

c. recovering said first and second Fab'-SH from said host cells; and d. forming covalent bonds between the free thiol cysteinyl residues of said first and second Fab'-SH to form bivalent F(ab')$_2$.

In embodiments of the invention, efficient directed disulfide bond formation occurs in vitro, utilizing directed covalent coupling methods known in the art whereby bispecific bivalent antibodies are produced. In particularly preferred embodiments, the disulfide bond formation between the first and second Fab'-SH comprises the following steps:

a. reacting the first Fab'-SH with (i) 5,5'-dithiobis (2-nitrobenzoic acid) (DTNB) to form a thionitrobenzoate derivative Fab'-TNB or (ii) a bifunctional maleimide;

b. directly coupling said first Fab'-TNB or maleimidated Fab' to the second Fab'-SH to form a F(ab')$_2$; and c. recovering said F(ab')$_2$.

Novel F(ab')$_2$ compositions are provided by the methods of this invention. Such compositions are a. essentially free of F(ab')$_2$ Fv regions containing cysteinyl residues with derivatized sulfhydryl groups, except for any native disulfide bond found in the native Fv regions, b. entirely free of F(ab')$_2$ having hinge region intrachain disulfide bonds, c. entirely free of contaminating arsenite, and d. entirely homogenous as to the heavy chain C-terminal amino acid residue.

In another embodiment, high level expression of immunoglobulins or fragments thereof in recombinant microbes is achieved by a method comprising culturing a host cell transformed with nucleic acid encoding an immunoglobulin polypeptide under the transcriptional control of an inducible promoter/operator system whereby expression of the polypeptide is repressed prior to induction sufficient to permit post-induction polypeptide levels in the cell culture of greater than about 1 gram of polypeptide per liter of cell culture. Typically, this is accomplished by using a powerful promoter such as phoA in a low copy number vector or in a host engineered to express levels of repressor sufficient to fully occupy all phoA operator sites and fully repress the operon.

DETAILED DESCRIPTION OF THE INVENTION

Definitions

Figure 1:
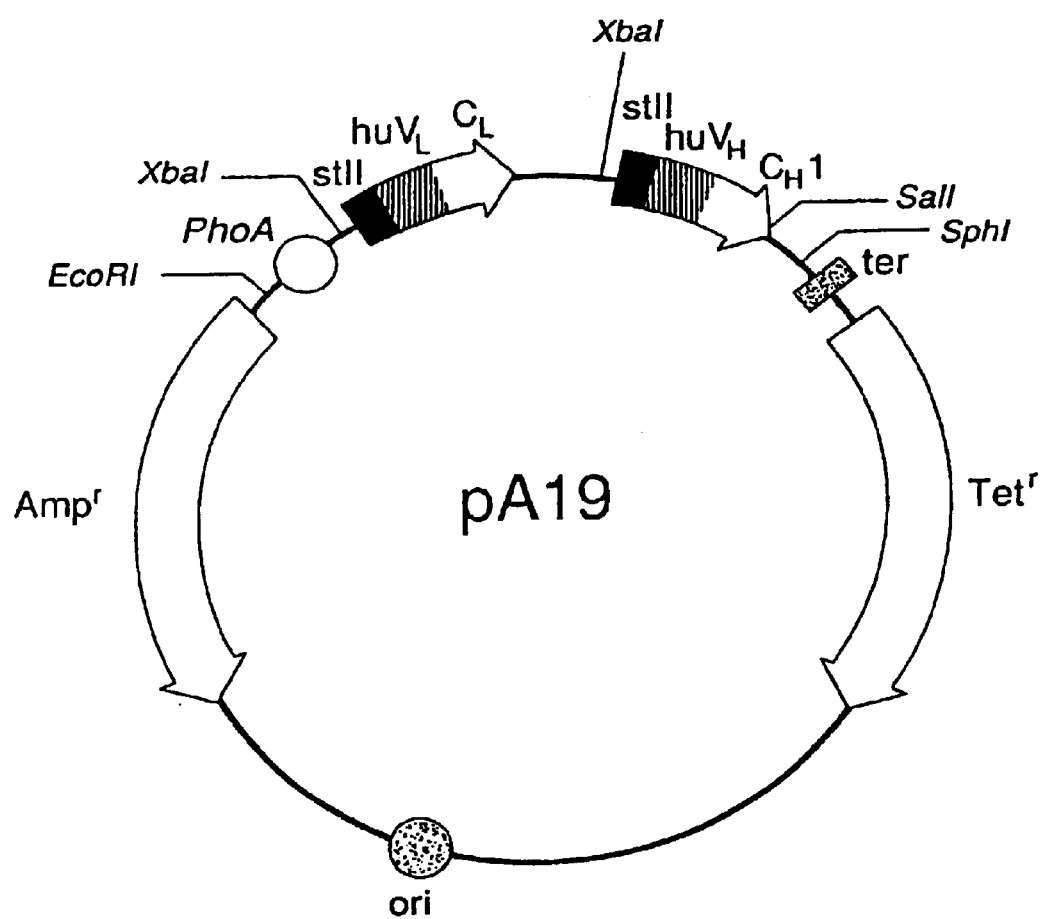
FIG. 1 shows the plasmid pA19 as used for the co-secretion of huMAb4D5-8 light chain and heavy chain Fd' fragment from E. coli. The Fab' expression unit is dicistronic with both chains under the transcriptional control of the PhoA promoter (C. N. Chang et al., *Gene* 44: 121 (1986)) which is inducible by phosphate starvation. The humanized variable domains (huV$_L$ and huv$_H$, P. Carter et al., *Proc. Natl. Acad. Sci. U.S.A.*, 89(10):4285–9 (1992)) are precisely fused on their 5' ends to a gene segment encoding the heat stable enterotoxin II (stII) signal sequence (R. N. Picken et al., *Infect. Immun.* 42: 269 (1983)) and on their 3' side to human $_1$ ($C_L$, W. Palm and N. Hilschmann, *Z. Physiol. Chem.* 356: 167 (1975)) and IgG1 ($C_H1$, J. W. Ellison et al., *Nucleic Acids Res.* 10: 4071 (1982)) constant domains respectively. The coding regions are separated by 83 base pairs and each is preceded by a ribosomal binding site (Picken et al., supra) to enable efficient initiation of translation. The Fab' expression unit was cloned into the Eco RI site of pBR322 (F. Bolivar et al., *Gene* 2: 95 (1977)) previously modified by removal of the Sal I and Sph I sites without changing the amino acid sequence of the tetracycline resistance gene product. Construction of different Fab' variants was facilitated by installing unique Sal I and Sph I sites towards the end of the $C_H1$ gene and immediately preceding the bacteriophage λ t$_0$ to transcriptional terminator (S. Scholtissek, et al., *Nucleic Acids Res.* 15: 3185 (1987)).

In general, the following words or phrases have the indicated definitions when used in the description, examples, and claims:

The term Fv is defined to be a covalently or noncovalently-associated heavy and light chain heterodimer which does not contain constant domains.

The term Fab' is defined herein as a polypeptide comprising a heterodimer of the variable domain and the first constant domain of an antibody heavy chain, plus the variable domain and constant domain of an antibody light chain, plus at least one additional amino acid residue at the carboxy terminus of the heavy chain $C_H1$ domain including one or more cysteine residues. F(ab')$_2$ antibody fragments are pairs of Fab' antibody fragments which are linked by a covalent bond(s).

The Fab' heavy chain may include a hinge region. This may be any desired hinge amino acid sequence. Alternatively the hinge may be entirely omitted in favor of one or more cysteine residues or, preferably a short (about 1–10 residues) cysteine-containing polypeptide. In certain applications, a common naturally occurring antibody hinge sequence (cysteine followed by two prolines and then another cysteine) is used; this sequence is found in the hinge of human IgG$_1$ molecules {E. A. Kabat, et al., *Sequences of Proteins of Immunological Interest* 3rd edition (National Institutes of Health, Bethesda, Md., 1987)}. In other embodiments, the hinge region is selected from another desired antibody class or isotype. In certain preferred embodiments of this invention, the C-terminus of the $C_H1$ of Fab' is fused to the sequence Cys X X. X preferably is Ala, although it may be any other residue such as Arg, Asp, or Pro. One or both X amino acid residues may be deleted.

The "hinge region" is the amino acid sequence located between $C_H1$ and $C_H2$ in native immunoglobulins or any sequence variant thereof. In the case of the humanized 4D5 antibody described infra, the hinge region is located between residues 224 (asp in . . . Cys Asp Lys . . . ) and 233 (Pro in . . . Cys Pro Ala). Analogous regions of other immunoglobulins will be employed, although it will be understood that the size and sequence of the hinge region may vary widely. For example, the hinge region of a human IgG1 is only about 10 residues, whereas that of human $IgG_3$ is about 60 residues.

The term Fv-SH or Fab'-SH is defined herein as a Fv or Fab' polypeptide having at least one cysteinyl free thiol. Preferably the free thiol is in the hinge region, with the light and heavy chain cysteine residues that ordinarily participate in inter-chain bonding being present in their native form. In the most preferred embodiments of this invention, the Fab'-SH polypeptide composition is free of heterogenous proteolytic degradation fragments. In certain embodiments, the Fab'-SH polypeptide is also substantially (greater than about 90 mole percent) free of Fab' fragments wherein heavy and light chains have been reduced or otherwise derivatized so as not to be present in their native state, e.g. by the formation of aberrant disulfides or sulfhydryl addition products. In alternative embodiments, the Fab'-SH has heavy and light chains which are not covalently coupled.

A humanized antibody for the purposes herein is an immunoglobulin amino acid sequence variant or fragment thereof which is capable of binding to a predetermined antigen and which comprises a FR region having substantially the amino acid sequence of a human immunoglobulin and a CDR having substantially the amino acid sequence of a non-human immunoglobulin or a sequence engineered to bind to a preselected antigen.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and transcriptional terminators. Particularly preferred are highly regulated inducible promoters that suppress Fab' polypeptide synthesis at levels below growth-inhibitory amounts while the cell culture is growing and maturing, for example, during the log phase.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in same reading frame. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean a nucleic acid sequence that is foreign to the cell, or homologous to the cell but in a position within the host cell nucleic acid in which the element is ordinarily not found.

As used herein, the expressions "cell" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations are will be clear from the contextually clear.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al, *Nucleic Acids Res.,* 9: 6103–6114 (1981), and Goeddel et al., *Nucleic Acids Res.* 8: 4057 (1980).

"Preparation" of DNA from cells means isolating the plasmid DNA from a culture of the host cells. Commonly used methods for DNA preparation are the large and small scale plasmid preparations described in sections 1.25–1.33 of Sambrook et al., (*Molecular Cloning: A Laboratory Manual* New York: Cold Spring Harbor Laboratory Press, 1989). DNA preparations are purified by methods well known in the art (see section 1.40 of Sambrook et al., supra).

Suitable Methods for Practicing the Invention

Typically a cultured microbial host cell is transformed with a vector comprising Fab'-encoding nucleic acid (i.e., nucleic acid encoding heavy chain Fd fragment and light chain) operably linked to control sequences recognized by the host cell transformed with the vector (hereafter, "Fab" will be referred to as a specific embodiment, but it will be understood that any Fv-containing antibody fragments or fusion/sequence derivative thereof can be used provided that a cysteine residue capable of forming a periplasmic free thiol is present in the Fv region or sequence fused thereto). The cells are cultured under conditions suitable for the secretion of Fab' into the periplasmic space of the host cell and formation of the free thiol. In general, a dicistronic operon is used to direct the co-expression of corresponding light and heavy chain fragments. Alternatively, separate chains are expressed from separate promoters on the same or different plasmids. Secondly, the Fab chains are preceded by signal sequences to direct secretion into the periplasmic space, where it is believed that the redox environment favors disulfide bond formation for assembly of the light and heavy chain fragments but not disulfide bond formation between hinge cysteine residues. In particularly preferred embodiments, the expression control sequence is the *E. coli* phoA promoter (C. N. Chang et al., *Gene* 44: 121 (1986)) inducible by phosphate starvation and the signal sequence is the heat-stable enterotoxin II signal sequence (R. N. Picken et al., *Infect. Immun.* 42: 269 (1983)).

It is currently preferred that the antibody fragments be expressed in bacterial cells grown at high cell density in a fermentor. Suitable fermentation conditions are described in the Example below.

The polypeptides containing free thiol are recovered from the fermentation media and/or recovered from freeze-thawed cells (typically by osmotic shock) and subsequently purified. Recovery (including purification) is most successful if the Fab'-SH is maintained in the protonated form. Other conditions for maintaining the protonated form include the use of organic solvents or other agents for shifting the pKa of dissociation of -SH. This is conveniently accomplished at acid pH, i.e., preferably 2 or more pH units below the pKa of the hinge or unpaired cysteinyl thiol. Alternatively, the Fab'-SH is reacted with a protective group such as TNB or p-methoxybenzyl in order to maintain the Fab' in a homogenous state suitable for further reaction. In yet another alternative, pyridine disulfide is added to the Fab'-SH to form a mixed disulfide; this stabilizes the free sulfhydryl until it is deprotected for coupling or other processing. In still another alternative embodiment, the free sulfhydryl is not protected but is reduced prior to coupling or further processing. Suitable protecting groups, known in the art, are described in E. Gross & J. Meiemhofer, *The Peptides: Analysis, Structure, Biology* Vol 3: Protection of Functional Groups in Peptide Synthesis (Academic Press, New York, 1981).

Affinity purification, such as on streptococcal protein G sepharose or staphylococcal protein A at acidic pH (typically, about pH 4 to pH 6, preferably about pH 5.0) is preferred. Alternatively, two-phase liquid extraction may be used. Small amounts of contaminating proteolytic fragments are readily removed by hydrophobic interaction chromatography, using, for example, silica gel and/or alkyl or aryl-substituted chromatography resins such as phenyl Toyopearl. It is preferred that a cocktail of protease inhibitors be used (such as phenylmethylsulfonyl fluoride (PMSF), leupeptin, pepstatin and/or benzemidine) to inactivate or inhibit host proteases, and to include a metal ion chelating agent such as EDTA in the culture and recovery procedures. The chelating agent is selected and included in an amount to prevent metal ion catalysis of disulfide bond formation.

In certain embodiments, Fab'-(SH)n(where n is equal to or greater than one) form $F(ab')_2$ in vivo during recombinant production. In these embodiments, the Fab'-(SH) amino acid sequence has been modified to contain preferably more than one cysteinyl residue. For example, $F(ab')_2$ having three disulfide bonds between heavy chains are recovered directly from an *E. coli* cell paste, following the culture in *E. coli* of Fab'-SH$_3$.

In other embodiments, $F(ab')_2$ is prepared from purified Fab'-(SH)$_n$ (where n is equal to or greater than one) by in vitro chemical coupling using cross-linking agents or adventitious oxidants such as dissolved oxygen. In the latter instance, purified Fab' will form $F(ab')_2$ due simply to air oxidation. In addition, bispecific $F(ab')_2$ is produced by the use of Fab'-SH derivatives which direct the coupling of discrete Fab' and prevent the formation of bivalent monospecific $F(ab')_2$. One suitable chemistry for mono- or bi-specific $F(ab')_2$ is that of Brennan et al., supra. A Fab'-TNB derivative is prepared in a similar manner to Fab'-SH, except that Fab'-SH released from freeze-thawed cells by osmotic shock is adjusted to about pH 7.5 in the presence of excess DTNB. Equimolar quantities of Fab'-SH and Fab'-TNB are coupled together efficiently to form the $F(ab')_2$ fragment by a disulfide exchange reaction in the presence of EDTA.

The linkless Fv, Fab', Fab'-SH and $F(ab')_2$ polypeptides of this invention do not have a disulfide bond between the light and heavy chains. Typically, the polypeptide is modified as the result of direct expression of a modified polypeptide, or by chemical or enzymatic means. Typical amino acid sequence modifications of the polypeptide involve substituting or deleting one or, preferably, both of the two cysteines which form the inter-chain (heavy-light) disulfide bond. Typically, these cysteines are replaced with serines, although it is within the scope hereof to covalently modify one or both of the cysteine side chain so as to be incapable of forming a disulfide bond.

One or both of the cysteines may be modified with fatty acids or other chemical groups and rendered incapable of forming a disulfide bond by a variety of known methods, including but not limited to the following methods: (1) covalent modification using dehydrating or activating agents such as N,N'-dicyclohexylcarbodiimide (DCC) or ethyoxy-ethoxycarbonyl-dihydroquinoline (EEDQ); (2) acylation, using ketenes, anhydrides, isothiocyanates, or beta-lactones; (3) carbamoylation using cyanates; (4) hemimercaptal or hemimercaptol formation using aldehydes and some keto acids; (5) alkylation and arylation, by addition to activated double bonds (using N-ethylmaleimide), by reactions with quinones, by reaction with haloacids and their amides (using iodoacetic acid, or alpha-bromo-hexadecanoic acid), by methylation reactions (such as with dimethylsulfate), by sulfoalkylation, by arylation (with nitrobenzene compounds), or by reaction with diazo compounds; (6) reaction with metal ions such as silver and organic mercury compounds such as mercuric chloride; (7) reaction with arsenic compounds; (8) reaction with sulfites; (9) oxidation reactions; and (10) reaction with sulfenyl halides to form mixed disulfides.

The polypeptide may be modified within a host cell, or as a post-translational modification to the recombinantly produced polypeptide. It is currently preferred that any post-translational modifications take place within 24, and preferably within a few hours of recovery from a host cell or microorganism.

Methods for detecting the presence of modifications to the cysteines of the polypeptides of this invention lung surfactant protein are commonly known, such as through the analysis of the mass spectra of a sample of the polypeptide. Alternatively, thin layer chromatography (TLC) is performed on a sample. While this approach to peptide analysis is common in the field, see e.g. Stuart and Young, *Solid Phase Peptide Synthesis*, pp 103–107, and 118–122, (Pierce Chem. Co., 2d ed., 1984).

In certain embodiments, there is a very strong interaction between the light and heavy chains such that eliminating the interchain disulfide does not result undesirable levels of dissociation between the light and heavy chains. The linkless Fab'-SH polypeptides advantageously allow homogeneous $F(ab')_2$ to be prepared by chemical coupling.

The Fab sequences of this invention are obtained from conventional sources of antibodies. Polyclonal antibodies to an antigen generally are raised in animals by multiple subcutaneous (sc) or intraperitoneal (ip) injections of the antigen and an adjuvant. It may be useful to conjugate the antigen or a fragment containing the target antigen amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The route and schedule of immunization of the animal or cultured antibody-producing cells therefrom are generally in keeping with established and conventional techniques for antibody stimulation and production. While mice are frequently employed as the test model, it is contemplated that any mammalian subject or antibody-producing cells obtained therefrom can be employed.

After immunization, monoclonal antibodies are prepared by recovering immune lymphoid cells—typically spleen cells or lymphocytes from lymph node tissue—from immunized animals and immortalizing the cells in conventional fashion, e.g. by fusion with myeloma cells or by Epstein-Barr (EB)-virus transformation and screening for clones expressing the desired antibody. The hybridoma technique described originally by Köhler, G. and Milstein, C., *Nature* 256: 52–53 (1975) has been widely applied to produce hybrid cell lines that secrete high levels of monoclonal antibodies against many specific antigens. Hybridomas secreting the desired antibody are identified by conventional methods. Routine methods are then employed to obtain DNA from hybridomas that encode the heavy and light chains of the selected antibody. Alternatively, one extracts antibody-specific messenger RNAs from B-cells of an immunized animal, reverse transcribes these into complementary DNA (cDNA), and amplifies the cDNA by PCR or by cloning it in a bacterial expression system. Another technique suitable for obtaining source heavy and light chain sequences uses a bacteriophage lambda vector system (which contains a leader sequence that secretes the expressed Fab protein into the periplasmic space) together with the generation and screening of great numbers of functional antibody fragments for those which demonstrate the desired activity. This system is commercially available.

Amino Acid Sequence Variants

This invention also encompasses amino acid sequence variants of the native Fab polypeptide sequences. These variants are prepared by introducing appropriate nucleotide changes into the DNA encoding the Fab or by in vitro synthesis of the desired Fab. Such variants include, for example, humanized variants of non-human antibodies, as well as deletions from, or insertions or substitutions of, residues within particular amino acid sequences. Any combination of deletion, insertion, and substitution can be made to arrive at the final construct, provided that the final construct possesses the desired characteristics. The amino acid changes also may alter post-translational processing of the target polypeptide, such as changing the number or position of glycosylation sites, introducing a membrane anchoring sequence into the constant domain or modifying the leader sequence of the native Fab.

In designing amino acid sequence variants of target polypeptides, the location of the mutation site and the nature of the mutation will depend on the target polypeptide characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the target polypeptide that are preferred locations for mutagenesis is called "alanine scanning mutagenesis" as described by Cunningham and Wells (*Science,* 244: 1081–1085 [1989]), and Duncan, A. R. and Winter, G. (*Nature,* 322: 738–740 (19881). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Thus, while the site for introducing an amino acid sequence variation is predetermined, the nature of the mutation per se need not be predetermined. For example, to optimize the performance of a mutation at a given site, Ala scanning or random mutagenesis may be conducted at the target codon or region and the expressed target polypeptide variants are screened for the optimal combination of desired activity.

There are two principal variables in the construction of amino acid sequence variants: the location of the mutation site and the nature of the mutation. In general, the location and nature of the mutation chosen will depend upon the target polypeptide characteristic to be modified.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the target polypeptide sequence) may range generally from about 1 to 10 residues, more preferably 1 to 5, most preferably 1 to 3. Examples of terminal insertions include fusion of a heterologous N-terminal signal sequence to the N-terminus of the Fv polypeptide to facilitate the secretion of the mature Fv polypeptide from recombinant host cells. Such signal sequences generally will be obtained from, and thus homologous to, the intended host cell species. Suitable sequences for *E. coli* include STII or Ipp.

Other insertional variants of the target polypeptide include the fusion to the N- or C-terminus of the target polypeptide of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989. Additional suitable polypeptide sequences include but are not limited to sequences derived from immunoglobulins, carrier proteins, receptors, growth factors, nutrient substances, cellular adhesive molecules, tissue-specific adhesion factors, enzymes, toxins and the like. These examples will be in addition to insertions of cysteine or cysteine-containing polypeptides such as hinge regions which provide free thiol cysteinyl.

Another group of variants are amino acid substitution variants. These variants have at least one amino acid residue in the immunoglobulin polypeptide removed and a different residue inserted in its place. The sites of greatest interest for substitutional mutagenesis include the CDRs, FR and hinge regions. They include substitutions of cysteine for other residue and insertions which are substantially different in terms of side-chain bulk, charge, and/or hydrophobicity. Other sites for substitution are described infra, considering the effect of the substitution of the antigen binding, affinity and other characteristics of a particular target antibody.

Fab itself is a deletional variant of intact immunoglobulin in which the heavy chain constant domain downstream from $C_H1$ is deleted. Further, in preferred embodiments the $C_H1$ domain is followed C-terminally by a cysteine-containing sequence such as Cys Ala Ala, or sequences having more than one Cys.

DNA encoding Fab amino acid sequence variants is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the target polypeptide or by total gene synthesis. These techniques may utilize target polypeptide nucleic acid (DNA or RNA), or nucleic acid complementary to the target polypeptide nucleic acid. Oligonucleotide-mediated mutagenesis is a preferred method for preparing substitution, deletion, and insertion variants of target polypeptide DNA.

PCR mutagenesis is also suitable for making amino acid variants of the Fab polypeptide. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al. *Gene,* 34: 315 [1985]). The starting material is the plasmid (or other vector) comprising the Fab DNA to be mutated. The codon(s) in the Fab polypeptide DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the Fab polypeptide DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated Fab polypeptide DNA sequence.

Insertion of DNA into a Vector

The cDNA or genomic DNA encoding the Fab polypeptide is inserted into a replicable vector for further cloning (amplification of the DNA) or for expression. Many vectors are available, and selection of the appropriate vector will depend on 1) whether it is to be used for DNA amplification or for expression of the encoded protein, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, a promoter, and a transcription termination sequence.

(a) Signal Sequence Component

In general, the signal sequence may be a component of the vector, or it may be a part of the target polypeptide DNA that is inserted into the vector. Included within the scope of this invention are Fab polypeptides with any native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native Fab polypeptide signal sequence, the signal sequence is substituted by a prokaryotic signal sequence selected, for example, from the group of the alkaline phosphatase, penicillinase, lpp, or heat-stable enterotoxin II leaders.

(b) Origin of Replication Component

Expression and cloning vectors may, but need not, contain a nucleic acid sequence that enables the Fab nucleic acid to replicate in one or more selected host cells. Generally, in cloning vectors this sequence is one that enables the vector to replicate independently of the host chromosomal DNA, and includes origins of replication or autonomously replicating sequences. Such sequences are well known for a variety of microbes. The origin of replication from the plasmid pBR322 is suitable for most Gram-negative bacteria.

DNA may also be replicated by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of the target polypeptide DNA. However, the recovery of genomic DNA encoding the target polypeptide is more complex than that of an exogenously replicated vector because restriction enzyme digestion is required to excise the target polypeptide DNA. Similarly, DNA also can be inserted into the genome of vertebrate and mammalian cells by conventional methods.

(c) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for *Bacilli*.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 2: 327 [1982]), mycophenolic acid (Mulligan et al., *Science*, 209: 1422 [1980]) or hygromycin (Sugden et al., *Mol. Cell. Biol.*, 5: 410–413 [1985]). The three examples given above employ bacterial genes under eukaryotic control to convey resistance to the appropriate drug G418 or noomycin (geneticin), xgpt (mycophenolic acid), or hygromycin, respectively.

(d) Promoter Component

Expression and cloning vectors will usually contain a promoter that is recognized by the host organism and is operably linked to the Fab polypeptide nucleic acid. Promoters are untranslated sequences located upstream (5') to the start codon of a the Fab structural gene (generally within about 100 to 1000 bp) that control its transcription and translation. Such promoters typically fall into two classes, inducible and constitutive. Inducible promoters are promoters that initiate increased levels of transcription from DNA under their control in response to some change in culture conditions, e.g. the presence or absence of a nutrient or a change in temperature.

Inducible promoters under high regulation are preferred for the microbial expression of Fv-containing polypeptides. At this time a large number of promoters recognized by a variety of potential host cells are well known. These promoters are operably linked to DNA encoding the Fab polypeptide by removing the promoter from the source DNA by restriction enzyme digestion and inserting the isolated promoter sequence into the vector. Both the native Fab polypeptide promoter sequence and many heterologous promoters may be used to direct amplification and/or expression of the Fab polypeptide DNA. However, heterologous promoters are preferred, as they generally permit greater transcription and higher yields of expressed target polypeptide as compared to the native target polypeptide promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21–25 [1983]). However, other known bacterial promoters are suitable. Their nucleotide sequences have been published, thereby enabling a skilled worker operably to ligate them to DNA encoding the target polypeptide (Siebenlist et al., *Cell*, 20: 269 [1980]) using linkers or adaptors to supply any required restriction sites. Promoters for use in bacterial systems also generally will contain a Shine-Dalgarno (S.D.) sequence operably linked to the DNA encoding the target polypeptide.

Construction of suitable vectors containing one or more of the above listed components employs standard ligation techniques. Isolated plasmids or DNA fragments are cleaved, tailored, and religated in the form desired to generate the plasmids required.

Selection and Transformation of Host Cells

Suitable host cells for expressing Fab are microbial cells such as yeast, fungi, and prokaryotes. Suitable prokaryotes include eubacteria, such as Gram-negative or Gram-positive organisms, for example, *E. coli*, *Bacilli* such as *B. subtillis*, *Pseudomonas* species such as *P. aeruginosa*, *Salmonella typhimurium*, or *Serratia marcescens*. One preferred *E. coli* cloning host is *E. coli* 294 (ATCC 31,446), although other strains such as *E. coli* B, *E. coli* X1776 (ATCC 31,537), *E. coli* RV308(ATCC 31,608) and *E. coli* W3110 (ATCC 27,325) are suitable. These examples are illustrative rather than limiting. Preferably the host cell should secrete minimal amounts of proteolytic enzymes, and additional protease inhibitors may desirably be incorporated in the cell culture.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Culturing the Host Cells

Cells used to produce the Fab polypeptide of this invention are cultured in suitable media as described generally in Sambrook et al., (*Molecular Cloning: A Laboratory Manual* New York: Cold Spring Harbor Laboratory Press, 1989). Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

It is currently preferred that the bacterial host cells be cultured at temperatures from 37° C. to 29° C., although temperatures as low as 20° C. may be suitable. Optimal temperatures will depend on the host cells, the Fab sequence and other parameters. 37° C. is generally preferred.

Purification of Fab Polypeptides

Soluble polypeptides are recovered from recombinant cell culture to obtain preparations that are substantially homogeneous as to Fab. As a first step, the culture medium or periplasmic preparation is centrifuged to remove particulate cell debris. Periplasmic preparations are obtained in conventional fashion, e.g. by freeze-thaw or osmotic shock methods, The membrane and soluble protein fractions are then separated. The Fab polypeptide is then purified from the soluble protein fraction. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; protein A or protein G affinity matrix (e.g. Sepharose) columns; and hydrophobic interaction chromatography.

Fab polypeptide variants in which residues have been deleted, inserted or substituted are recovered in the same fashion, taking account of any substantial changes in properties occasioned by the variation. For example, preparation of a Fab polypeptide fusion with another protein or polypeptide, e.g. a bacterial or viral antigen, facilitates purification since an immunoaffinity column containing antibody to the antigen is used to adsorb the fusion. Immunoaffinity columns such as a rabbit polyclonal anti-target polypeptide column can be employed to absorb the target polypeptide variant by binding it to at least one remaining immune epitope. A protease inhibitor also is useful to inhibit proteolytic degradation during purification, and antibiotics may be included to prevent the growth of adventitious contaminants.

Utility of the Fab-containing Polypeptides

The antibody fragments of this invention are useful in diagnostic assays for antigen in specific cells, fluids or tissues, for immunoaffinity purification of the antigens and for therapies which are based on antigen antagonism.

Analytical methods for the antigen bound by the Fab polypeptide are conventional and may use a label bound to the Fab. The label used with the Fab polypeptide is any detectable functionality that does not interfere with its binding to Fab. Numerous labels are known, including the radioisotopes $^{32}P$, $^{35}S$, $^{14}C$, $^{125}I$, $^{3}H$, and $^{131}I$, fluorophores such as rare earth chelates or fluorescein and its derivatives, rhodamine and its derivatives, dansyl, umbelliferone, luceriforases, e.g., firefly luciferase and bacterial luciferase (U.S. Pat. No. 4,737,456), luciferin, 2,3-dihydrophthelazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotiniavidin, spin labels, bacteriophage labels, stable free radicals, imaging radionuclides (such as Technetium) and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., Nature, 144: 945 (1962); David et al., Biochemistry, 13: 1014–1021 (1974); Pain et al., J. Immunol. Methods, 40: 219–230 (1981); and Nygren, J. Histochem. and Cytochem., 30: 407–412 (1982). Preferred labels herein are enzymes such as horseradish peroxidase and alkaline phosphatase. The conjugation of such label, including the enzymes, to the Fab-containing polypeptide is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147–166. Such bonding methods are suitable for use with the Fab polypeptides of this invention.

The Fab-containing polypeptides also may comprise an immunotoxin. For example, the Fab heavy chain is optionally conjugated to a cytotoxin such as ricin for use in AIDS therapy. Alternatively, the toxin may be a cytotoxic drug or an enzymatically active toxin of bacterial, fungal, plant or animal origin, or an enzymatically active fragment of such a toxin. Enzymatically active toxins and fragments thereof include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaoneria officinalis inhibitor, gelonin, mitogellin, restrictocin, phenomycin, enomycin and the tricothecanes. In another embodiment, the antibodies are conjugated to nonpeptidyl drugs such as cis-platin or SFU. Conjugates of the monoclonal antibody and such cytotoxic moieties are made using a variety of bifunctional protein coupling agents. Examples of such reagents are SPDP, IT, bifunctional derivatives of imidoesters such as dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate and bis-active fluorine compounds such as 1,5-difluoro-2,4-dinitrobenzene. The lysing portion of a toxin may be joined to the Fab antibody fragment.

Immunotoxins can be made in a variety of ways, as discussed herein. Commonly known crosslinking reagents can be used to yield stable conjugates.

When used in vivo for therapy, the Fab-containing fragments of the subject invention are administered to the patient in therapeutically effective amounts (i.e. amounts that have desired therapeutic effect) in the same fashion as intact immunoglobulins. The products prepared in accord with the methods of this invention offer the advantage of substantial molecular homogeneity and are devoid of toxic contaminants heretofore used in preparing $F(ab')_2$.

The antibody compositions used in therapy are formulated and dosages established in a fashion consistent with good medical practice taking into account the disorder to be treated, the condition of the individual patient, the site of delivery of the composition, the method of administration and other factors known to practitioners. The antibody compositions are prepared for administration according to the description of preparation of polypeptides for administration, infra.

EXAMPLE

Expression of Active Fab, Fab', and $F(ab')_2$ Antibody Fragments

Overexpression of the HER2 proto-oncogene product ($p185^{HER2}$) has been associated with a variety of aggressive human malignancies. An Escherichia coli expression system has been developed that secretes functional Fab and Fab' fragments of a humanized antibody, huMAb4D5-8, at titers of about 1 to in excess of about 2 grams per liter as judged by binding to antigen, $p185^{HER2}$. The Fab' fragment was recovered with the single hinge region cysteine present mainly as the free thiol (up to about 90 mole %) permitting efficient directed disulfide bond formation in vitro to form the bivalent $F(ab')_2$ antibody fragment. This molecule is indistinguishable from $F(ab')_2$ derived from proteolysis of intact antibody in antigen binding affinity and in antiproliferative activity against the human breast tumor cell line, SK-BR-3, which over-expresses $p185^{HER2}$, but unlike the proteolytic product, the $F(ab')_2$ here is C-terminally homogenous. This invention facilitates the construction of monospecific and bispecific $F(ab')_2$ antibody fragments, including naturally derived or humanized antibody fragments for research and therapeutic purposes. This invention is particularly applicable for developing antibody fragments capable of directing diagnostic or therapeutic moieties to target antigens such as tumor foci characterized by overexpression of the HER2 proto-oncogene The murine monoclonal antibody known as muMAb4D5 (Fendly, B. M. et al., Cancer Res. 50:1550–1558 (1990)) is directed against the extracellular domain (ECD) of $p185^{HER2}$, The muMAb4D5 and its uses are described in copending PCT application WO 89106692 published 27 Jul. 1989. This murine antibody was deposited with the ATCC and designated ATCC CRL 10463. In this description, the terms muMAb4D5, chMAb4D5 and huMAb4D5 represent murine, chimerized and humanized versions of the monoclonal antibody 4D5, respectively.

muMAb4D5 has potential for clinical intervention in that it specifically inhibits the growth of human tumor cell lines overexpressing $p185^{HER2}$ (2, 3) and is rapidly internalized by target cells (data not shown). Amplification and/or overexpression of HER2 is associated with multiple human malignancies and appears to be integrally involved in progression of 25–30% of primary human breast and ovarian cancers (5). The muMAb4D5 molecule was previously "humanized" (6) in an attempt to improve its clinical efficacy by reducing immunogenicity and allowing it to support human effector functions. The humanized antibody, huMAb4D5-8, contains essentially only the antigen binding loops from the murine parent antibody together with human variable region framework residues and constant domains. This humanized antibody has 3-fold higher affinity for p185$^{HER2}$ ECD than the murine parent, comparable anti-proliferative activity against p185$^{HER2}$ overexpressing tumor cells and supports antibody-dependent cellular cytotoxicity.

It was desired to enlarge the repertoire of anti-p185$^{HER2}$ antibody reagents to include the Fab and F(ab')$_2$ antibody fragments of huMAb4D5-8. The smaller size of these fragments compared to the intact antibody is likely to enhance their specific localization to solid tumors by improving tumor penetration and promoting more rapid removal from serum (reviewed in ref. 8). huMAb4D5-8 Fab and F(ab')$_2$ fragments were obtained by direct recombinant expression to facilitate engineering of these fragments. Furthermore this strategy provided more homogeneous preparations of antibody fragments than could be obtained by limited proteolysis and partial reduction of intact antibodies (reviewed in ref. 9). Functional Fv and Fab fragments had been secreted from *E. coli* (10).

The strategy here for the *E. coli* secretion of antibody fragments (FIG. 11) shares two basic similarities with the work of others (10). Firstly a dicistronic operon is used to direct the co-expression of corresponding light and heavy chain fragments. Secondly the antibody chains are preceded by bacterial signal sequences to direct secretion into the periplasmic space of *E. coli* where the redox environment favors disulfide bond formation and the light and heavy chain fragments may assemble. The system here differs from earlier strategies in three basic ways. Firstly the transcription unit utilizes the a highly regulated promoter, the *E. coli* PhoA promoter (11) inducible by phosphate starvation, and heat-stable enterotoxin II signal sequence (12). Secondly, the gene segment for the light chain precedes that for the heavy chain Fd fragment (V$_H$ and C$_H$1 domains). Thirdly, in order to express the Fab' fragment of huMAb4D5-8 the C$_H$1 gene segment was extended to encode part of the cysteine-containing antibody hinge region. The sequence Cysteine followed by two Prolines and another Cysteine (CPC terminus) was initially chosen since it is found in the hinge region of human IgG$_1$ molecules (17) including the full length version of huMAb4D5-8 (6). The construction of additional Fab' variants by cassette mutagenesis (18) of the pBR322-based expression vector was facilitated by installing unique Sal I and Sph I restriction sites towards the end of the C$_H$1 gene segment and immediately 3' to the stop codon, respectively.

The huMAb4D5-8 Fab fragment was expressed in a phage resistant derivative of *E. coli* RV308 (19) grown at high cell density in a fermentor (20). The titer of functional huMAb4D5-8 Fab in fermentation media is routinely 1 to 2 grams per liter as judged by p185$^{HER2}$ ECD binding ELISA (6). Modest amounts of huMAb4D5-8 Fab (usually <200 mg/l) are found associated with the cell paste and may be released by osmotic shock. The consensus framework region of the huMAb4D5-8 Fab fragment was found to bind tightly to both staphylococcal protein A and to streptococcal protein G, allowing their use for affinity purification. Very similar estimates of titers are obtained for culture media or cell paste samples after affinity purification on protein A prior to antigen-binding ELISA. Similar expression titers of p185$^{HER2}$ ECD binding activity have been obtained for the huMAb4D5-8 Fab variant (cysteine, two prolines and another cysteine) and the additional Fab' variant described below.

Formation of F(ab')$_2$ molecules requires chance encounters of Fab' hinge cysteinyl thiols to form disulfide bonds without the assistance of extensive interactions between C$_H$3 domains possible in the case of intact antibodies. Thus high level expression of Fab' in the periplasmic space of *E. coli* was anticipated to drive formation of F(ab')$_2$ in vivo. In fact <10% of the Fab' molecule having the CPC terminus (isolated from either media or cell paste) were recovered as the bivalent form as judged by SDS-PAGE analysis after protein A purification. High resolution mass spectrometry and other studies suggested that substantial formation of an intramolecular disulfide bond between the two hinge cysteine residues had occurred. This possibility was precluded by the construction of an additional Fab' variant with a single hinge cysteine residue having the C-terminal sequence, Cys Ala Ala. Negligible quantities of F(ab')$_2$ are formed when this Fab' variant is secreted from *E. coli* and DTNB analysis does not detect free thiol.

The Fab' molecules are recovered under conditions that maintain the hinge cysteine present as the free thiol and then readily and efficiently formed into F(ab')$_2$ by directed coupling in vitro. For example, Brennan et al. (23) reacted a Fab' free thiol (Fab'-SH) with DTNB to form the thionitrobenzoate derivative (Fab'-TNB) which was then coupled to a second Fab'(Fab'-SH) to form the bispecific F(ab')$_2$. The following strategy allows the routine purification of intact functional huMAb4D5-8 Fab' Cys Ala Ala variant with 75–90% of the molecules containing a free hinge thiol as judged by DTNB analysis (FIG. 2): firstly, growth conditions were judiciously modified (20) to target secretion of Fab' to the periplasmic space of *E. coli* rather than into the culture media where the Fab' hinge thiol was found to be quantitatively and covalently blocked. Secondly, the Fab' fragment was isolated from the cell paste and affinity purified on protein G sepharose at low pH (pH 5.0) to maintain the cysteinyl thiol in the less reactive protonated form. Thirdly, EDTA was added to chelate metal ions capable of catalyzing disulfide bond formation and to inactivate metello proteases. Finally a cocktail of additional protease inhibitors (phenylmethylsulfonyl fluoride (PMSF), leupeptin, pepstatin and benzamidine) virtually eliminated proteolysis of Fab' by *E. coli* proteases during the purification. Small amounts of contaminating proteolytic fragments in Fab' preparations were readily removed by hydrophobic interaction chromatography. The Fab'-TNB derivative was prepared in a similar manner except that Fab'-SH released from freeze-thawed cells by osmotic shock was adjusted to neutral pH in the presence of excess DTNB.

Figure 2:
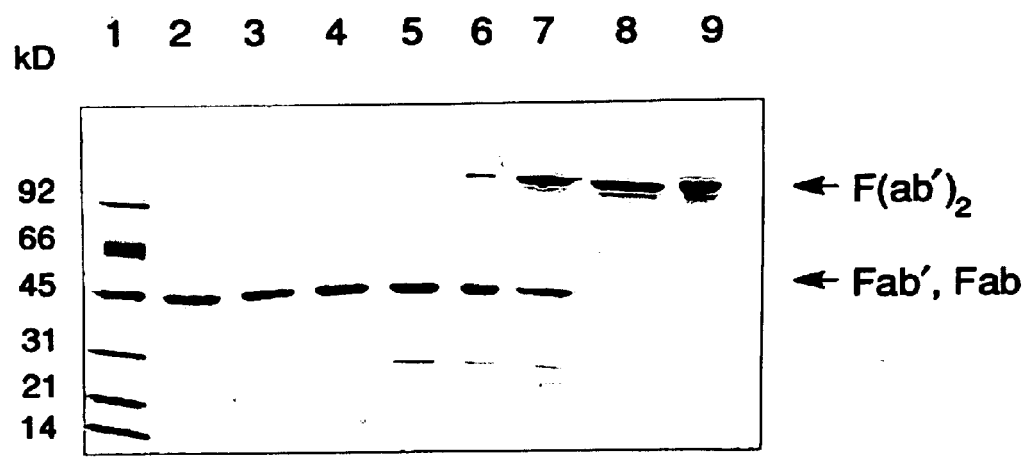
FIG. 2 shows the purification of the Fab, Fab' and F(ab')$_2$ (Cys Ala Ala variant) fragments of huMAb4D5-8. Proteins were analyzed by SDS-PAGE on a 4 to 20% gel under non-reducing conditions with Coomassie brilliant blue (R250). Samples shown are protein molecular weight markers (lane 1), Fab (lane 2); Fab'-SH before (lane 3) and after (lane 4) a mock coupling reaction; Fab'-TNB before (lane 5) and after (lane 6) a mock coupling reaction; Fab'-SH coupled with Fab'-TNB (lane 7), F(ab')$_2$ purified by gel filtration (lane 8) and F(ab')$_2$ derived from limited pepsin digestion (E. Lamoyi, et al., *Methods Entymol.* 121: 652 (1986)) of full length huMAb4D5-8 expressed in mammalian cells (P. Carter et al., *Proc. Natl. Acad. Sci. U.S.A.* (1992) supra (lane 9). Antibody fragments (2 μg per sample) were reacted with 4 mM iodoacetamide prior to electrophoresis. The huMAb4D5-8 Fab fragment was purified from fermentation supernatants by centrifugation to remove cell debris, DEAE sepharose ion exchange chromatography end then affinity purified using protein A CL 4B or protein G sepharose. HuMAb4D5-8 Fab'-SH was purified by thawing 15 g cell paste in the presence of 21 ml of 100 mM sodium acetate (pH 3.5), 10 mM EDTA, 0.2 mM PMSF, 5 μM popstatin, 5 μM leupeptin, 2.4 mM benzamidine. Cell debris was removed by centrifugation (40,000 g, 10 min, 4° C.). The resultant supernatant (pH 5.0) was passed over DEAE sepharose and loaded on to a 2 ml protein G sepharose column. Protein eluted with 100 mM sodium acetate (pH 3.5), 10 mM EDTA was adjusted to pH 4.0 in the presence of 1.5M (NH$_4$)$_2$SO$_4$ and loaded on to 2 ml phenyl Toyopearl column. Fab'-SH was eluted with 20 mM sodium acetate (pH 4.0), 0.8 M (NH$_4$)$_2$SO$_4$, 10 mM EDTA, reduced in volume by ultrafiltration (Centriprep-10, Amicon) and buffer exchanged into 10 mM sodium acetate (pH 5.0), 10 mM EDTA by G25 gel filtration. The Fab thionitrobenzoate derivative was prepared in a similar manner except that the DEAE flow through was adjusted to 5 mM DTNB and pH 7.5. The total concentration of huMAb4D5-8 Fab and Fab' variants was determined from the measured absorbance at 280 nm and the extinction coefficient determined by amino acid composition analysis ($\epsilon^{0.1\%}$=1.56). The free thiol content of huMAb4D5-8 Fab'-SH was determined by analysis with DTNB as described (T. E. Creighton, *Protein Structure, a Practical Approach* (IRL Press, Oxford, UK, 1990), p. 157), whereas the TNB content of huMAb4D5-8 Fab'-TNB was determined by the yield upon reduction with dithiothreitol. Equimolar quantities of huMAb4D5-8 Fab'-TNB (by TNB content) and Fab'-SH (by -SH content) were coupled at a combined concentration of ≧1.4 mg/ml in the presence of 100 mM tris-HCl (pH 7.5) and 10 mM EDTA for 1 hour at 37° C. HuMAb4D5-8 F(ab')$_2$ was isolated from the coupling reaction by S100-HR gel filtration (Pharmacia) in the presence of phosphate-buffered saline. The F(ab')$_2$ samples were passed through a sterile 0.2 μm filter and stored either at 4° C. or flesh frozen in liquid nitrogen and stored at −70° C.

Equimolar quantities of Fab'-SH and Fab-TNB were coupled together to efficiently form the F(ab')$_2$ antibody fragment by a disulfide exchange reaction (FIG. 2). The coupling reaction was followed by monitoring the increase in absorbance at 412 nm upon release of the thionitrobenzoate anion and found to reach completion after 30 to 60 min at 37° C. No free thiol was detected in the reaction mix after coupling and the amount of remaining Fab' is consistent with that amount of unreactive material in the Fab'-SH and Fab'-TNB preparations. F(ab')$_2$ was separated from Fab' by gel filtration on a S100-HR sizing column. Only trace quantities of huMAb4D5-8 F(ab')$_2$ are were formed in mock coupling reactions containing either Fab'-SH or Fab'-TNB alone, as anticipated (23).

The physical and chemical integrity of purified huMAb4D5-8 Fab and F(ab')$_2$ was evaluated by SDS-PAGE (FIG. 2), analysis of the amino terminal sequence, amino acid composition plus free thiol content, and by circular dichroism. Purified huMAb4D5-8 Fab ($M_r$=47.7 kdal) and F(ab')$_2$ ($M_r$=96.0 kdal) fragments analyzed by SDS-PAGE under non-reducing conditions each gave a single major band of the expected mobility. After SDS-PAGE under reducing conditions both Fab and F(ab')$_2$ antibody fragments gave a doublet of bands of similar intensities as expected from release of stoichiometric quantity of free light chain (23.4 kdal) and heavy chain Fd (24.3 kdal) or Fd' (24.6 kdal) fragments (not shown). Amino terminal sequence analysis (8 cycles) of Fab and F(ab')$_2$ antibody fragments gave the expected mixed sequence from a stoichiometric 1:1 mixture of light and heavy chains ($V_L/V_H$) Asp/Glu, Ile/Val, Gln/Gln, Met/Leu, Thr/Val, Gln/Glu, Ser/Ser, and Pro/Gly with no evidence of additional sequences. No free thiol was detected in either Fab or F(ab')$_2$ preparations by DTNB analysis as expected. Amino acid analysis (27) of acid hydrolysed Fab or F(ab')$_2$ was in excellent agreement with the expected composition (6). The circular dichroism spectrum of the Fab fragment is characteristic of an immunoglobulin fold.

The function of huMAb4D5-8 Fab and F(ab')$_2$ antibody fragments was investigated by measuring the binding affinity for the p185$^{HER2}$ ECD and by investigating their effect upon the proliferation of the p185$^{HER2}$ overexpressing human breast carcinoma line, SK-BR-3 (Table 1).

TABLE 1

Analysis of huMAb4D5-8 fragments by p185$^{HER2}$ ECD binding affinity and anti-proliferative activity with breast carcinoma, SK-6R-3 cells.

| huMAb4D5-8 variant | Source | $K_d$, pM | Relative cell proliferation[†] |
|---|---|---|---|
| Fab | E. coli | 570 | 91 |
| F(ab')$_2$[‡] | E. coli | 290 | 53 |
| F(ab')$_2$ | 293 cells | 300 | 50 |

*$K_d$ values for the p185$^{HER2}$ ECD were determined as previously described (5) and the standard error of the estimates are $\leq \pm 10\%$.
[†]Proliferation of SK-BR-3 cells incubated for 96 hr with huMAb4D5 variants shown as a percentage of the untreated control as described (5). Data represent the maximal anti-proliferative effect for each variant calculated as the mean of triplicate determinations at a fragment concentration of 10 μg/ml. Data are all taken from the same experiment and the estimated standard error $\leq \pm 15\%$.
[‡]Cys Ala Ala variant.

The binding affinity of huMAb4D5-8 F(ab')$_2$ antibody fragment for p185$^{HER2}$ ECD is identical to that of the corresponding fragment derived from limited proteolysis of whole antibody expressed in mammalian cells. The bivalent F(ab')$_2$ antibody fragment derived from E. coli has identical anti-proliferative activity with SK-BR-3 cells to both the intact bivalent huMAb4D5-8 parent antibody derived from 293 cells (6) and the F(ab')$_2$ antibody fragment derived from limited pepsin digestion of intact antibody. In contrast, the monovalent Fab molecule does not significantly affect the growth of SK-BR-3 cells. This suggests that the crosslinking of p185$^{HER2}$ on the surface of cells may be required for inhibiting their proliferation. It appears exceedingly unlikely that the 2-fold weaker antigen binding affinity of the Fab compared to the F(ab')$_2$ could account for the lack of anti-proliferative activity of the Fab at concentrations up to several hundred fold above the $K_d$. Furthermore, it is possible to block the anti-proliferative activity of the bivalent parent antibody, muMAb4D5, with a monovalent huMAb4D4 Fab fragment.

In this example, the expression titer of functional Fab fragments was increased compared to the reports in the literature for E. coli, from about 1000-fold to 1 to 2 grams per liter. Additionally, Fab' molecules were recovered. This enhanced expression is very likely due only in part to the higher cell densities (10 to 20-fold) and more precisely controlled environment of the fermentor then the simple shake flask, the very tight control of pre-induction expression and the characteristics of the humanized variable domain sequence employed. The titer of Fab' obtained here using the phoA promoter are surprisingly high and may result from a combination of the use of this powerful promoter in a low copy number (pBR322-based) vector. Thus the repressor is not titered to less effective levels. The cells also could be transformed to make surplus repressor. What is important is that the promoter be inactive prior to induction. It is possible that vector design and the high thermal stability of the Fab fragment ($T_M$>80° C.) also may be important. This system should greatly facilitate clinical or biophysical studies requiring large quantities of antibody fragments.

Similar high expression levels have been observed for several additional variants of huMAb4D5-8 Fab which contain one or more amino acid changes in the antigen binding loops or nearby framework residues (6). Two alternative antigen-binding specificities have been recruited into huMAb4D5-8 Fab' by judicious replacement of antigen binding residues and found to give high expression titers. This is consistent with the notion that the framework of a polypeptide comprising substantially huMAb4D5-8 Fab' might be generically useful for highly expressed humanized Fab' molecules.

The huMAb4D5-8 Fab' Cys Ala Ala shows very little tendency to form F(ab')$_2$ in vivo despite the apparently quantitative formation of intra-domain disulfides in the variable regions. However, in vitro F(ab')$_2$ forms readily by air oxidation of Fab'-SH at pH 7.5 in the absence of EDTA at concentrations that are at least 10-fold lower than are found in vivo.

Without committing to any particular mechanism, it is believed that the redox potential of the periplasmic space of E. coli is sufficiently oxidizing to allow formation of the intra-domain disulfide bonds but not the inter-heavy chain disulfide which is presumably thermodynamically less favorable. Nevertheless, recovery of functional Fab' fragments secreted into the periplasmic space of E. coli with the unpaired hinge cysteine mainly as the free thiol provides the essential starting material for directed coupling (23, 32, 33). We have additionally exploited the free thiol for immobilization of the huMAb4D5-8 Fab' fragment on an activated thiol support as previously described (34), enabling the p185$^{HER2}$ ECD to be affinity purified from solution. The free hinge thiol has also been used for attachment of fluorescent probes for fluorescence-activated cell sorting. It is also within the scope of this invention to use the free cysteinyl thiol for the site-directed attachment of radionuclides for imaging or therapy. This would offer the advantage over conventional labelling strategies of a defined stoichiometry and attachment site without the risk of compromising antigen binding affinity.

Bibliography

1. B. M. Fendly et al., Cancer Res. 50: 1550 (1990).
2. R. M. Hudziak et al., Molec. Cell. Biol. 9: 1165 (1989).
3. R. Lupu et al., Science 249: 1552 (1990).
5. D. J. Slamon et al., Science 235: 177 (1987); D. J. Slamon et al., Science 244:707 (1989).

6. P. Carter et al., *Proc. Natl. Acad. Sci. U.S.A.* 89(10): 4285–9 (1992).
7. P. T. Jones et al., *Nature* 321: 522 (1986); L. Riechmann et al., *Nature* 332: 323 (1988); M. Verhoeyen et al., *Science* 239: 1534 (1988).
8. R. D. Blumenthal et al., *Adv. Drug Del. Rev.* 4: 279 (1990).
9. P. Parham in *Cellular Immunology* (E. M. Weir, Ed. Blackwell Scientific, CA) 4th edition, vol 1 chapter 14 (1983).
10. A. Skerra and A. Plückthun, *Science* 240: 1038 (1988); M. Better et al., ibid p. 1041.
11. C. N. Chang et al., *Gene* 44: 121 (1986).
12. R. N. Picken et al., *Infect. Immun.* 42: 269 (1983).
13. W. Palm and N. Hilschmann, *Z. Physiol. Chem.* 366: 167 (1975).
14. J. W. Ellison et al., *Nucleic Acids Res.* 10: 4071 (1982).
15. F. Bolivar et al., *Gene* 2: 95 (1977).
16. S. Scholtissek, et al., *Nucleic Acids Res.* 15: 3185 (1987)
17. E. A. Kabat, et al., *Sequences of Proteins of Immunological Interest* 3rd edition (National Institutes of Health, Bethesda, Md., 1987).
18. J. A. Wells et al., *Gene* 34: 315 (1985).
19. R. A. Maurer, Ph.D. thesis, Harvard University (1978).
20. The huMAb4D5-8 Fab' fragment was expressed in *E. coli* strain 25F2 derived from the strain RV308 (ref. 22, ATCC#31608) by inactivating the tonA gene. Cells were grown for 32–40 hours in an aerated 10 liter fermentor at 37° C. at a low agitation rate (650 rpm, Kla ~600 mmol $l^{-1}$ $hr^{-1}$ $atm^{-1}$) in a medium that initially contained 12 g $l^{-1}$ digested casein, 17 mM glucose, 2.4 mM isoleucine hydrochloride, 47 mM $(NH_4)_2SO_4$, 10 mM $NaH_2PO_4$, 18 mM $K_2HPO_4$, 4.1 mM trisodium citrate, 12 mM $MgSO_4$, 125 μM $FeCl_3$ and 20 μM each of $ZnSO_4$, $MnSO_4$, $CuSO_4$, $CoCl_2$, $H_3B_3$ and $NaMoO_4$) plus 12 mg $l^{-1}$ tetracycline and received automated feeds of ammonia to maintain the pH at 7.0 and also glucose to maintain a slight excess or avoid anaerobisis depending upon cell density of 80 to 100 $OD_{550}$. The cell density at harvest is usually 120 to 150 $OD_{550}$.
21. G. L. Ellman, *Arch. Biochem. Biophys.* 82: 70 (1959).
23. M. Brennan et al., *Science* 229: 81 (1985).
24. E. Lamoyi, et al., *Methods Enzymol.* 121: 652 (1986).
25. T. E. Creighton, *Protein Structure, a Practical Approach* (IRL Press, Oxford, UK, 1990), p. 157.
26. P. Matsudaira, *J. Biol. Chem.* 262: 10035 (1987)
27. S. Moore and W. H. Stein, *Methods Enzymol.* 6: 819 (1963)
32. M. J. Glennie et al., *J. Immunol.* 139: 2367 (1987); M. J. Glennie et al., *J. Immunol.* 141: 3662 (1988).
33. T. Nitta et al., *J. Immunol.* 19; 1437 (1989). T. Nitta et al., *Lancet* 335: 368 (1990).
P. Carter and J. A. Wells, *Science* 237: 394 (1987).

What is claimed is:

1. A method for the production of a Fab' antibody fragment coupled to a heterologous molecule, comprising the steps of:
   (a) expressing nucleic acid encoding a Fab' antibody fragment in a prokaryotic host cell culture comprising the nucleic acid such that the Fab' is secreted to a periplasmic space of a prokaryotic host cell;
   (b) recovering the Fab' from the host cell culture, wherein the recovered Fab' comprises a CH1 fused to the amino acid sequence of CysXX, wherein X is Ala, Arg, Asp, or Pro, and wherein the cysteine of Cys XX is present as a free thiol, and the amount of the Fab' recovered from the host cell culture exceeds the amount of F(ab')$_2$ recovered therefrom; and
   (c) coupling the cysteine of CysXX that is present as a free thiol of the recovered Fab' to a heterologous molecule.

2. The method of claim 1 wherein the Fab' is recovered from host cell culture medium or a periplasmic preparation in step (b).

3. The method of claim 1 wherein a metal ion chelating agent is present during the recovery of the Fab'.

4. The method of clam 3 wherein the metal ion chelating agent is EDTA.

5. The method of claim 1 wherein a protease inhibitor is present during the recovery of the Fab'.

6. The method of claim 1 wherein the prokaryotic host cell is an *E. coli* cell.

7. The method of claim 1 wherein the recovered Fab' is able to be covalently bonded to a second Fab' to form a functional F(ab')$_2$.

8. The method of claim 1 wherein the Cys XX sequence has an amino acid sequence of CAA.

9. The method of any of claim 1, wherein the heterologous molecule is a different Fab'.

10. The method of any of claim 1, wherein the heterologous molecule is a detectable label, cytotoxic drug, toxin, or solid support.

11. The method of any of claim 1, wherein the heterologous molecule is a radionuclide or a fluorescent probe.

* * * * *

UNITED STATES PATENT AND TRADEMARK OFFICE
CERTIFICATE OF CORRECTION

PATENT NO. : 7,018,809 B1
APPLICATION NO. : 08/199268
DATED : March 28, 2006
INVENTOR(S) : Carter It is certified that error appears in the above-identified patent and that said Letters Patent is hereby corrected as shown below:

Front page, (56) References Cited, Other Publications, Sambrook et al. reference: "Spring Haron Lab." should read --Spring Harbor Lab.--

Page 3, second Parham reference: "Vitro produciton of a hybrid" should read --Vitro production of a hybrid--

Col. 7, line 16: "of huMAb4D5-8 light chain" should read --of huMAb4D5-8 κ light chain--

Col. 7, line 26: "side to human $_1$" should read --side to human $κ_1$--

Col. 13, line 66: "738-740 (19881)." should read --738-740 (1988).--

Col. 17, line 6: "*Genet.*, 2: 327" should read --*Genet.*, 1: 327--

Col. 17, line 11: "G418 or noomycin" should read --G418 or neomycin--

Col. 19, line 57: "or SFU." should read --or 5FU.--

Col. 20, line 56: "application WO 89106692" should read --application WO 89/06692--

Col. 23, line 33, Table 1: "SK-6R-3 cells." should read --SK-BR-3 cells.--

Col. 26, line 40, claim 9: "method of any of claim 1" should read --method of claim 1--

UNITED STATES PATENT AND TRADEMARK OFFICE
CERTIFICATE OF CORRECTION

PATENT NO. : 7,018,809 B1
APPLICATION NO. : 08/199268
DATED : March 28, 2006
INVENTOR(S) : Carter It is certified that error appears in the above-identified patent and that said Letters Patent is hereby corrected as shown below:

Col. 26, line 42, claim 10: "method of any of claim 1" should read --method of claim 1--

Col. 26, line 45, claim 11: "method of any of claim 1" should read --method of claim 1--

Signed and Sealed this

Fifth Day of September, 2006

JON W. DUDAS
*Director of the United States Patent and Trademark Office*